United States Patent [19]
Feild et al.

[11] Patent Number: 6,052,615
[45] Date of Patent: Apr. 18, 2000

[54] METHOD AND APPARATUS FOR SENSING AND ANALYZING ELECTRICAL ACTIVITY OF THE HUMAN HEART USING A FOUR ELECTRODE ARRANGEMENT

[75] Inventors: Dirk Q. Feild, Simi Valley; Hosmel Galan, Camarillo, both of Calif.

[73] Assignee: Zymed Medical Instrumentation, Inc., Camarillo, Calif.

[21] Appl. No.: 09/136,056

[22] Filed: Aug. 17, 1998

[51] Int. Cl.$^7$ .................................................. A61N 5/0402
[52] U.S. Cl. .......................................... 600/509; 600/512
[58] Field of Search ..................... 600/509, 512

[56] References Cited

U.S. PATENT DOCUMENTS

| | | |
|---|---|---|
| 3,991,747 | 11/1976 | Stanly et al. . |
| 4,106,495 | 8/1978 | Kennedy . |
| 4,478,223 | 10/1984 | Allor ........................................ 600/512 |
| 4,569,357 | 2/1986 | Sanz et al. . |
| 4,697,597 | 10/1987 | Sanz et al. ............................... 600/512 |
| 4,850,370 | 7/1989 | Dower ..................................... 600/512 |
| 5,458,116 | 10/1995 | Egler ....................................... 600/512 |
| 5,840,038 | 11/1998 | Xue et al. ................................ 600/512 |

OTHER PUBLICATIONS

"An Accurate, Clinically Practical System For Spatial Vectorcardiography", by Ernest Frank, Ph.D., Circulation, vol. XIII, May, 1956, p.p. 737 to 748.

"On Deriving the Electrocardiogram From Vectorcardiographic Leads", by G.E. Dower, M.D., et al., Clinical Cardiology, vol. 3, Apr. 1980, p.p. 87 to 95.

"A Clinical Comparison of Three VCG Lead Systems Using Resistance–Combining Networks", by G.E. Dower, M.B., et al, American Heart Journal, St. Louis, vol. 55, No. 4, Apr., 1958, p.p. 523 to 534.

A Lead Synthesizer For The Frank System to Simulate The Standard 12–Lead Electrocardiogram, by Gordon E. Dower, M.B., Journal of Electrocardiology, vol. 1, No. 1, p.p. 101 to 116, 1968.

"XYZ Data Interpreted by a 12–Lead Computer Program Using The Derived Electrocardiogram", by Gordon E. Dower, M.B., et al., Journal of Electrocardiology, vol. 12, No. 3, 1979, p.p. 249 to 261.

"The ECGD: A Derivation of The ECG From VCG Leads", by Gordon E. Dower, M.D., Journal of Electrocardiology, vol. 17, No. 2, 1984, p.p. 189 to 192.

*Primary Examiner*—Carl H. Layno
*Attorney, Agent, or Firm*—Kelly Bauersfeld Lowry & Kelley LLP

[57] ABSTRACT

A method of sensing and analyzing electrical activity of the human heart comprises the sensing of voltage signals generated by the heart between four electrodes (E, A, S and I) located at key positions on the surface of a subject's body. The E electrode is attachable to the anterior midline of the subject body at a level selected from the group consisting of the fourth rib interspace and the fifth rib interspace. The A and I electrodes are attachable to the subject's body on opposed sides of the anterior midline below the level of the E electrode but high enough so they are positioned over the subject's ribs or intercostal spaces. The S electrode is positioned over the subject's manubrium sterni. Signal processing means combines and scales the voltage signals to produce xyz vectorcardiographic signals, electrocardiographic signals corresponding to the lead signals of a 12-lead electrocardiograph, or both.

14 Claims, 4 Drawing Sheets

METHOD AND APPARATUS FOR SENSING AND ANALYZING ELECTRICAL ACTIVITY OF THE HUMAN HEART USING A FOUR ELECTRODE ARRANGEMENT

FIELD OF THE INVENTION

This invention relates to electrophysiology, and more particularly to instrumentation and methods for sensing and analyzing activity of the human heart.

BACKGROUND OF THE INVENTION

Over the last several decades, a variety of diagnostic procedures have been developed for sensing and analyzing activity of the human heart. These include electrocardiography, vectorcardiography and polarcardiography, all of which depend upon related instrumentation used to produce records derived from voltages produced by the heart on the surface of the human body.

The records so produced are graphical in character and require interpretation and analysis to relate the resulting information to the heart condition of the patient or other subject. Historically, such records have been produced directly as visible graphic recordings from wired connections extending from the subject to the recording device(. With advances in computer technology, it has become possible to produce such records in the form of digitally stored information for later replication of retrieval and analysis. Likewise, with advances in communication technology, remote (wireless) sensing has become possible.

(a) Electrocardiography

The production of a conventional 12-lead electrocardiogram (ECG) involves the placement of 10 lead electrodes (one of which is a ground or reference electrode) at selected points on the surface of a subject's body. Each electrode acts in combination with one or more other electrodes to detect voltages produced by depolarization and repolarization of individual heart muscle cells. The detected voltages are combined and processed to produce 12 tracings of time varying voltages. The tracings so produced are as follows:

| Lead | Voltage | Lead | Voltage |
| --- | --- | --- | --- |
| I | $vL - vR$ | V1 | $v1 - (vR + vL + vF)/3$ |
| II | $vF - vR$ | V2 | $v2 - (vR + vL + vF)/3$ |
| III | $vF - vL$ | V3 | $v3 - (vR + vL + vF)/3$ |
| aVR | $vR - (vL + vF)/2$ | V4 | $v4 - (vR + vL + vF)/3$ |
| aVL | $vL - (vR + vF)/2$ | V5 | $v5 - (vR + vL + vF)/3$ |
| aVF | $vF - (vL + vR)/2$ | V6 | $v6 - (vR + vL + vF)/3$ | where, in the standard, most widely used system for making short term electrocardiographic recordings of supine subjects, the potentials indicated above, and their associated electrode positions, are:

vL potential of an electrode on the left arm;

vR potential of an electrode on the right arm;

vF potential of an electrode on the left leg;

v1 potential of an electrode on the front chest, right of sternum in the 4th rib interspace;

v2 potential of an electrode on the front chest, left of sternum in the 4th rib interspace;

v4 potential of an electrode at the left mid-clavicular line in the 5th rib interspace;

v3 potential of an electrode midway between the v2 and v4 electrodes;

v6 potential of an electrode at the left mid-axillary line in the 5th rib interspace;

v5 potential of an electrode midway between the v4 and v6 electrodes;

vG (not indicated above) is a ground or reference potential with respect to which potentials vL, vR, vF, and v1 through v6 are measured. Typically, though not necessarily, the ground or reference electrode is positioned on the right leg.

Correct interpretation of an ECG requires a great deal of experience since it involves familiarity with a wide range of patterns in the tracings of the various leads. Any ECG which uses an unconventional system of leads necessarily detracts from the body of experience that has been developed, in the interpretations of conventional ECGs, and may therefore be considered generally undesirable. The tracings generated would be understandable only by a relative few who were familiar with the unconventional system.

Nevertheless, other lead systems have evolved from improvements in instrumentation that have permitted extension of electrocardiography to ambulatory, and even vigorously exercising subjects—and to recordings made over hours, or even days. F:or example, in stress testing the electrodes are moved from the arms to the trunk, although the same number of electrodes (10) are used. The tracings I, II, III, aVR, aVL and aVF are altered by this modification.

Although a 12-lead ECG is considered to be a cost effective heart test, it is to be noted that the relatively large number of electrodes required play an important role in determining costs—not only in terms of the direct cost of the electrodes themselves, but also terms of the time required to properly position and fix each electrode to a subject's body.

(b) Vectorcardiography

The pattern of potential differences on a body surface resulting from electrical activity of the heart can be mathematically approximated by replacing the heart with a dipole equivalent cardiac generator. The magnitude and orientation of this dipole are represented by the heart vector which is continually changing throughout the cycle of the heart beat. The XYZ coordinates of the heart give rise to time varying xyz signals, which may be written out as xyz tracings. Orthogonal leads to give these tracings were developed by Ernest Frank (see An Accurate, *Clinically Practical System For Spatial Vectorcardiography,* Circulation 13: 737, May 1956). Frank experimentally determined the image surface for one individual, and from this proposed a system using seven electrodes on the body, plus a grounding electrode. The conventional letter designations for such electrodes, and their respective positions were:

E at the front midline;

M at the back midline;

I at the right mid-axillary line;

A at the left mid-axillary line;

C at a 45° angle between the front midline and the left mid-axillary line;

F on the left leg;

H on the back of the neck. The first five electrodes (E, M, I, A and C) were all located at the same transverse level—approximately at the fourth of the fifth rib interspace. A linear combining network of resistors attached to these electrodes gave suitably scaled x, y and z voltage signals as outputs.

Unfortunately, xyz tracings are not as easy to interpret as 12 lead ECGs. However, Frank intended his system for a different purpose: vectorcardiography.

Vectorcardiography abandons the horizontal time coordinate of the ECG in favour of plots or tracings of the orientation and magnitude of the heart vector on each of three planes: a frontal (xy) plane plotting an x-axis (right arm to left arm) against a y-axis (head to foot); a transverse (xz) plane plotting the x-axis against a z-axis (front to back), and a sagittal plane plotting the y-axis against the z-axis.

Although it has long formed a basis for teaching electrocardiography, vectorcardiography has never become widely used. The technique was demanding and the system of electrode placement was different from that required for the ECG. Extra work was required, and it would still be necessary to record a 12-lead ECG separately with a different placement of electrodes.

An alternative to the Frank lead system that required only four active electrodes (R(right arm), A, F, E), and that used a resistor network based on Frank's image surface data was proposed in 1958 by G. E. Dower and J. A. Osborne (see *A Clinical Comparison of Three VCG Lead Systems Using Resistance-Combining Networks*, Am Heart J 55: 523, 1958). However, the xyz signals produced were sometimes different from those of Frank's lead system, and the RAFE system was not adopted.

(c) Polarcardiography

An alternative representation of the heart vector, known as polarcardiography, has been exploited since the early 1960's (see G. E. Dower, *Polarcardiography*, Springfield, Ill., Thomas, 1971). It has certain inherent advantages in defining abnormalities, and forms the basis of a successful program for automated analysis. Based on xyz signals, polarcardiography employs the Frank lead system. In order to render it competitive with the established 12-lead ECG, the lead vector concept has been employed to derive a resistor network that would linearly transform the xyz signals into analogs of the 12-lead ECG signals (see G. E Dower, *A Lead Synthesizer for the Frank Lead System to Stimulate the Standard* 12-*Lead Electrocardiogram*, J. Electrocardiol 1: 101, 1968, G. E. Dower, H. B. Machado, J. A. Osborne, *On Deriving the Electrocardiogram From Vectorcardiographic Leads*, Clin Cardiol 3: 97, 1980; and G. E. Dower, The ECGD: *A Derivation of the ECG from VCG leads* (ecitorial), J. Electrocardiol 17: 189,1984). The ECG thus derived is commonly referred to as the ECGD. Because the ECGD can be acceptable to an interpreting physician, it is not necessary for the technician to apply the electrodes required for a conventional ECG. Further, associated computer facilities can make vectorcardiograms and other useful displays available from the xyz recordings. Nevertheless, the number of electrodes called for by the Frank lead system are required. In addition, the effort required by the technician recording the xyz signals is about the same as for a conventional ECG.

(d) The Dower EASI lead system

An improved method and apparatus for sensing and analyzing activity of the human heart, and which requires a reduced number of electrodes to produce accurate simulations of conventional 12-lead electrocardiograms and vectorcardiograms, is described in U.S. Pat. No. 4,850,370 (the contents of which are incorporated herein). There, the A and I electrodes (the second and third electrodes) are described as being on opposite sides of the anterior midline at the same level as the first electrode (the E electrode). However, over the years it has been noted that the signal coming from the A-I electrode pair often contains a higher than desirable level of electrical artifact, probably generated by the nearby pectoral muscles.

Accordingly, there remains a need for an improved method and apparatus for sensing and analyzing activity of the human heart, and which requires a reduced number of electrodes similar to the Dower EASI lead system, which minimizes extraneous myoelectric potentials. The present invention fulfills these needs and provides other relate,d advantages.

SUMMARY OF THE INVENTION

It has been found that accurate simulations of 12-lead electrocardiograms can be derived by measuring and processing voltages sensed using 4 electrodes strategically placed on the surface of a subject's body. Although a fifth or grounding electrode may also be required, this will depend on the equipment used and may be avoided with suitable equipment.

As will become apparent, it is also possible to derive vectorcardiograms using the same 4 electrode placements. Indeed, in one implementation of the present invention, 12-lead electrocardiographic signals are derived from xyz vectorcardiography signals, the latter of which are derived from voltages sensed using the basic 4 electrodes. With this implementation, the derivation of vectorcardiographic signals may be seen as an intermediate result or step. However, as will be seen hereinafter, while the intermediate derivation of xyz vectorcardiographic signals is possible, it is not essential to the derivation of 12-lead electrocardiographic signals.

The 4 electrode positions that are fundamental in the use of the present invention consist of electrode position E of the Frank lead system, a modified electrode position A of the Frank lead system, an electrode position S over the upper end of the sternum (manubrium sterni), and a modified electrode position I of the Frank lead system. (Such E, A, S and I electrodes are from time-to-time collectively referred to herein as the "EASI" electrodes.) Specifically, the A and I electrodes are attached to the subject's is body on opposed sides of the anterior midline below the level o)f the E electrode but high enough so they are positioned over the subjects's ribs or intercostal spaces. Preferably, the A and I electrodes are positioned at the mid-axillary line, 2.5 centimeters below the level of the E electrode.

It has been found that 12-lead electrocardiographic signals and xyz vectorcardiographic signals can be derived by measuring and, with suitable signal processing means, combining and scaling the voltages present between first, second and third selected pairs of the EASI electrodes.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENT

FIGS. 1, 2, 3 and 4, each depicting a generalized signal processing means or signal processor 100, 200, 300 or 400, as the case may be, serve to illustrate the placement of EASI electrodes on the surface of a subject's body at positions E, A, S and I as hereinbefore described. (In this drawing, the letters E, A, S and I are used not only to identify positions on the human body but also electrodes at such positions.)

The electrodes themselves are common, widely available electrodes used in the process of taking ECGs, VCGs and the like. Their respective positions E, A, S and I serve to avoid the limbs and other undesirable sites such as the C, M and H positions (in the region of the left nipple, the back, and the head or lower neck) as used by Frank. Further, they give good signals with relatively little noise.

In contrast with the Dower EASI lead system described in U.S. Pat. No. 4,850,370, the A and I electrodes are attachable to the subject's body on opposed sides of the anterior midline below the level of the E electrode but high enough so they are positioned over the subject's ribs or intercostal spaces. It is important that the A and I electrodes not be so low that they are positioned over the fleshy areas below the ribs because such positioning also produces excessive electrical artifact. Preferably, the A and I electrodes are positioned at the mid-axillary line, 2.5 centimeters below the level of the E electrode. Such changes in electrode position, in comparison with the Dower EASI system, have minimal impact on the vectoral characteristics of the recorded signals by minimizing extraneous myoelectric potentials. Moreover, all of the advantageous feature's of the Dower EASI system remain intact, as discussed below.

Figure 1:
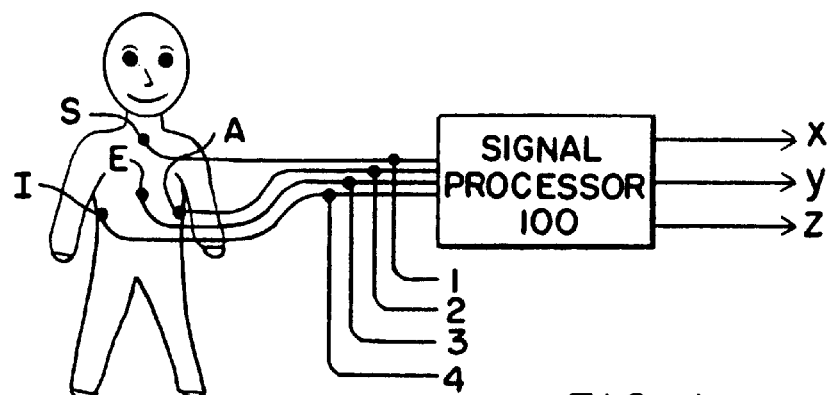
FIG. 1 illustrates the modified EASI electrode arrangement with signal processing for deriving xyz vectorcardiographic signals.

FIG. 1 illustrates a generalized signal processor 10 receiving EASI electrode signals (via wire connections 1, 2, 3 and 4) as an input, and producing xyz vectorcardiographic signals as an output.

Figure 2:
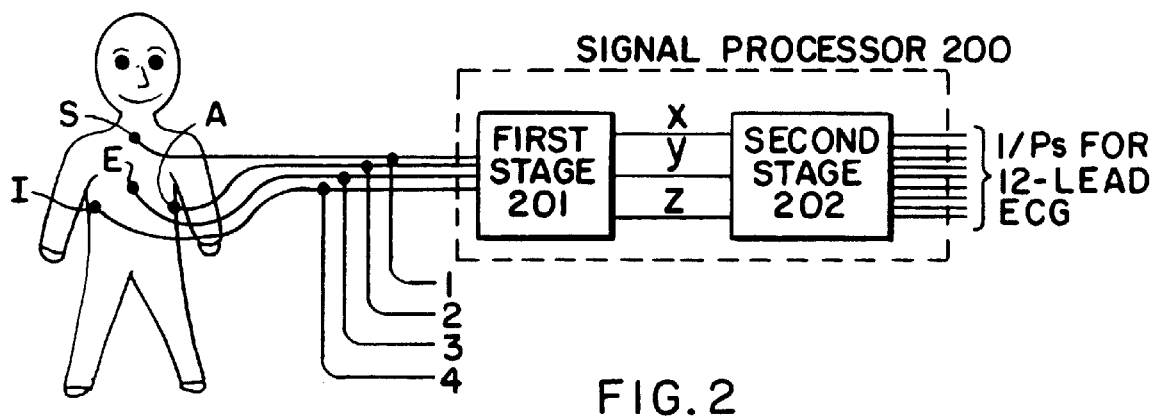
FIG. 2 illustrates the modified EASI electrode arrangement with signal processing for deriving 12-lead electrocardiographic signals, xyz vectorcardiographic signals being derived at an intermediate stage.

FIG. 2 illustrates a signal processor 200 having a first stage 201 and a second stage 202. In this case, nine output signals are derived to serve as inputs for producing a 12-lead ECG. At the intermediate stage of the output of stage 201 and the input of stage 202, xyz vectorcardiographic are produced. FIG. 2 recognizes that 12-lead electrocardiographic signals may be derived from xyz vectorcardiographic signals. This is of course the basis for the ECGD described above and is not a new observation per se. However, the derivation of 12-lead electrocardiographic signals from derived xyz vectorcardiographic signals produced in the manner indicated through stage 201 in FIG. 2 is considered new by Dower. In principle, it will be noted that there is no fundamental difference between signal processor 100 of FIG. 1 and first stage 201 of signal processor 200 in FIG. 2

Figure 3:
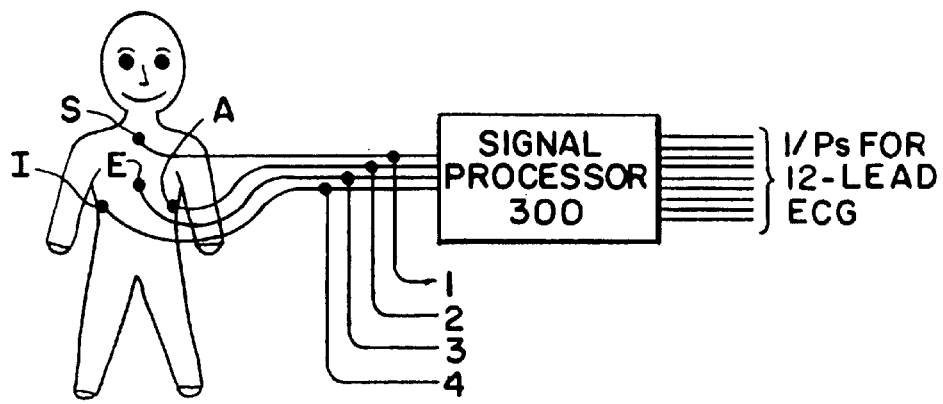
FIG. 3 illustrates the modified EASI electrode arrangement with signal processing deriving 12-lead electrocardiographic signals.

As will become apparent hereinafter, the signal processing means that are used in the implementation of the present invention comprise linear voltage combining and scaling networks. This is true of signal processor 100 in FIG. 1, and is also true of stages 201 and 202 of signal processor 200 shown in FIG. 2. Given this premise, it will be readily apparent to those skilled in the art that stages 201 and 202 in FIG. 2 may in fact be condensed into a single stage. FIG. 3 highlights the fact that this may be done. Here, signal processor 300 derives 12-lead electrocardiographic signals directly from EASI electrode signal inputs, and there is no necessary production of derived intermediate xyz vectorcardiographic signals as in the case of signal processor 200. Implicitly, signal processor 300 could include such a facility, but it is not essential.

Figure 4:
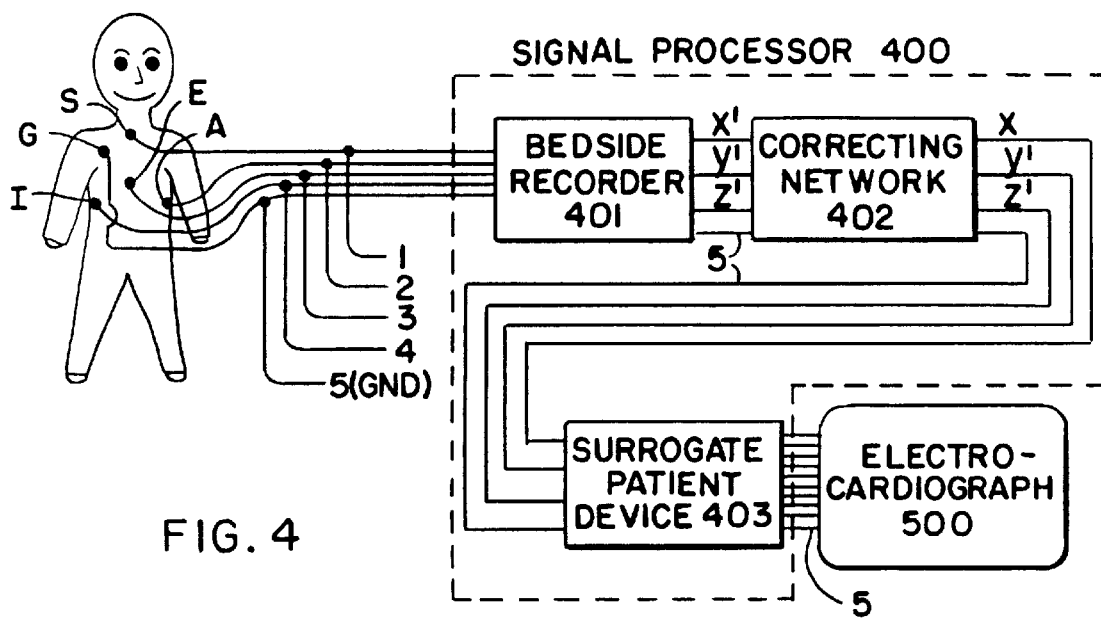
FIG. 4 illustrates in more detail a signal processing means for deriving vectorcardiographic and electrocardiographic signals from EASI electrodes.

FIG. 4, like FIG. 2, shows means for deriving both vectorcardiographic and electrocardiographic signals from EASI electrodes, signal processor 400 of FIG. 4 performing essentially the same function as signal processor 200 of FIG. 2. Additionally, FIG. 4 illustrates connection to an electrocardiograph 500. A fifth or grounding electrode G is also shown in FIG. 4, as is a ground line or path generally designated 5. The placement of grounding electrode G is not critical; it may be placed anywhere convenient—though typically on a subject's chest as indicated in FIG. 4. In any given case, the necessity for a grounding electrode and a ground line will depend on the equipment utilized. FIG. 4 illustrates such elements because they were used in the particular case now to be described in more detail.

Signal processor 400 comprise a bedside recorder 401, a correcting network 402, and a surrogate patient device 403. The combination of recorder 401 and correcting network 402 may be thought of as a first stage 201 in FIG. 2. Surrogate patient device 403 may be thought of as a second stage 202 in FIG. 2. Recorder 401, correcting network 402, and surrogate patient device 403 all act as linear voltage combining and scaling networks.

A preliminary point of note is that bedside recorder 401 and surrogate patient device 403 as stand alone elements are essentially well known devices. The exemplary recorder illustrated is a TOTEMITE™ Bedside Recorder, which embodies a processing network to derive conventional xyz vectorcardiographic signals in accordance with Frank (see above) and which is commonly used to record such signals on magnetic tape. When used in the manner indicated in FIG. 4, signals normally directed to magnetic tape (and which are normally xyz signals) are tapped to provide input signals (x'y'z') for correcting network 402. This is representationally shown in FIG. 5(a) which depicts a Frank network 405 as an included part of bedside recorder 401, but wired at the input to receive four EASI electrode signals. Conventional use of the Frank network is illustrated in FIG. 5(b) which shows each of the network's seven input terminals A, C, E, I, M, H and F present for the purpose of receiving inputs from each of seven corresponding A, C, E, I, M, H and F electrodes (not shown) located at corresponding A, C, E, I, M, H and F positions on a subject (also not shown).

Figure 6:
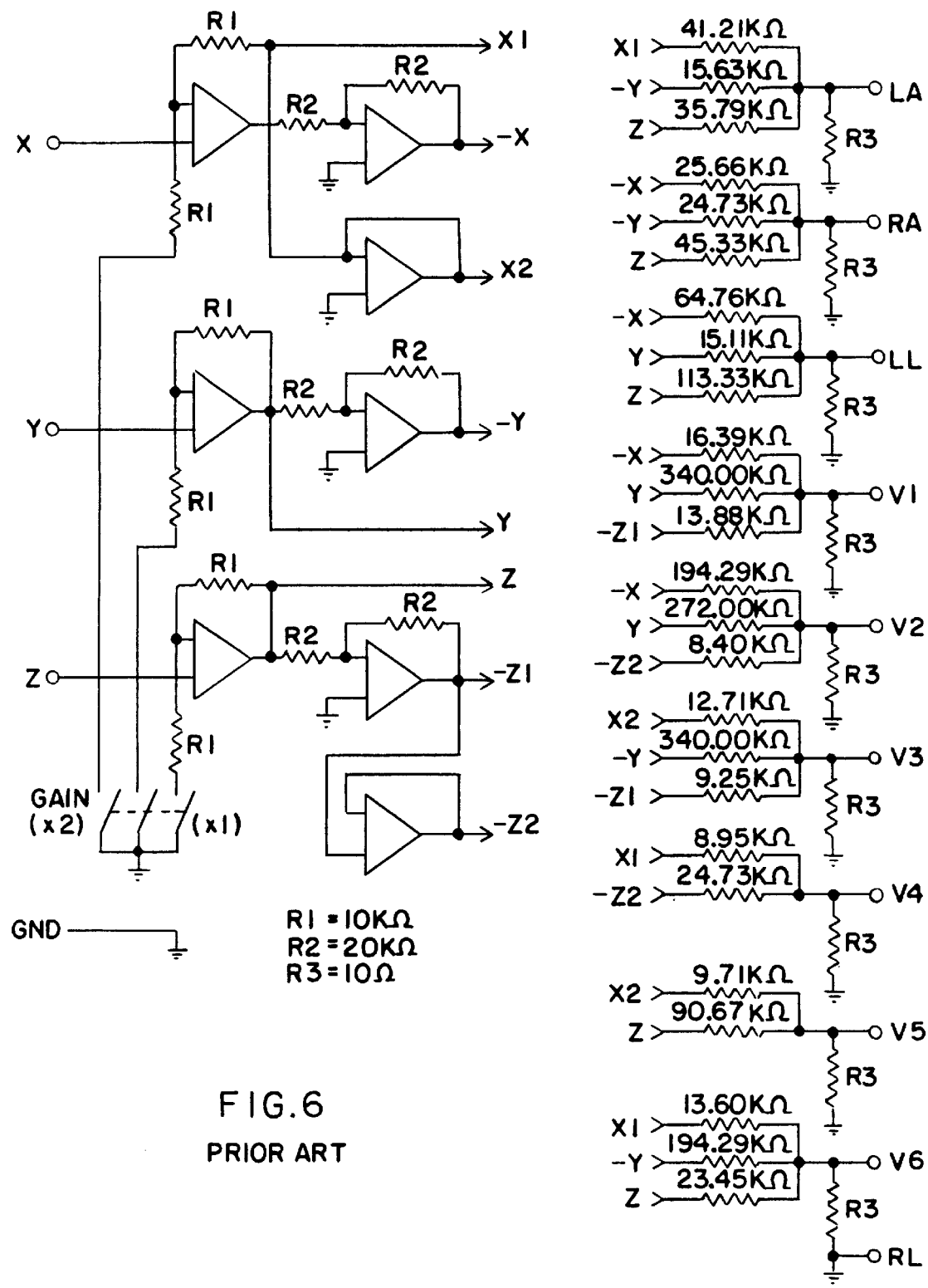
FIG. 6 is a prior art circuit diagram of a surrogate patient device which forms part of the signal processing means in FIG. 4.

Surrogate patient device 403, is a linear processing network whose outputs are scaled to match those that electrocardiographic 500 would "see" from electrodes attached to a subject for a conventional ECG. The design of such networks is known, the result being an ECGD. FIG. 6 illustrates prior art circuitry used to provide the action of a surrogate patient monitor. Since such design is known it will not be described here in any detail. However, it may be noted that the circuit arrangement shown in FIG. 6 is essentially disclosed in XYZ *Data Interpreted by a* 12-*Lead Computer Program Using the Derived Electrocardiogram,* J. Electrocardiol 12: 249, 1979 (by G. E. Dower and H. B. Machado). In that disclosure, signals again taken from a TOTEMITE Bedside Recorder (but using the Frank network forming part of the recorder "normally" to obtain xyz vectorcardiographic signals) were amplified by a factor of 1000 and applied to the XYZ terminal inputs of the surrogate patient device. In the environment of the present invention as shown in FIG. 4, the bedside recorder still receives xyz vectorcardiographic signal inputs; the difference now is that they are not received directly c,s an amplified output of the bedside recorder, but instead as the output of correcting network 402.

Referring again to FIG. 4 and FIG. 5(a), it can be appreciated that EASI electrode E is connected not only to input E of the Frank network 405, but also input C of the Frank network. Likewise, EASI electrode A is connected not only to input A of the Frank network, but also input M. EASI electrode I is connected not only to input I of the Frank network, but also input F. EASI electrode S is connected to input H of the Frank network. By reason of the departure from the 7 electrodes normally providing input to the Frank network, and by reason of the differing input configuration to the Frank network, it follows naturally that one would not expect the usual xyz vectorcardiographic signals at the output of the network.

More particularly, the conventional input/output signal relationship with a Frank network is:

$$V_X = 0.610 V_A + 0.171 V_C - 0.781 V_I \quad (1)$$

$$V_Y = 0.655 V_P + 0.354 V_M - 1.000 V_H \quad (2)$$

$$V_Z = 0.133 V_A + 0.736 V_M - 0.264 V_I - 0.374 V_E - 0.231 V_C \quad (3)$$

$V_x$, $V_y$ and $V_z$ appear as potential differences at the three paired outputs of Frank network 500 in FIG. 5(b), $V_A$, $V_C$ and $V_I$, etc. are measured with respect to an arbitrary reference of potential chosen by Frank. Any one of the seven electrodes of the Frank lead system could have been selected as the reference potential.

Figure 5A:
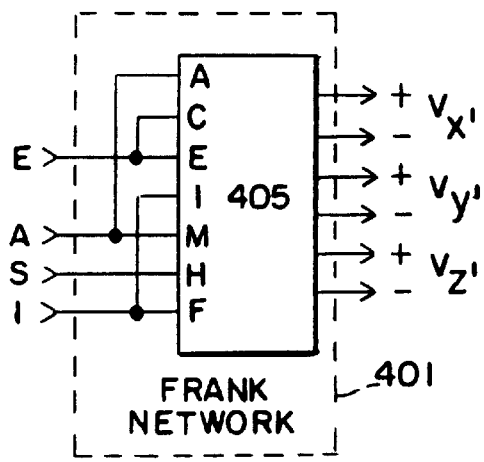
FIG. 5(a) representationally depicts a Frank network forming part of the bedside recorder shown in FIG. 4, the input of such network being configured to receive signals from the modified arrangement of EASI electrodes in accordance with the present invention.
Figure 5B:
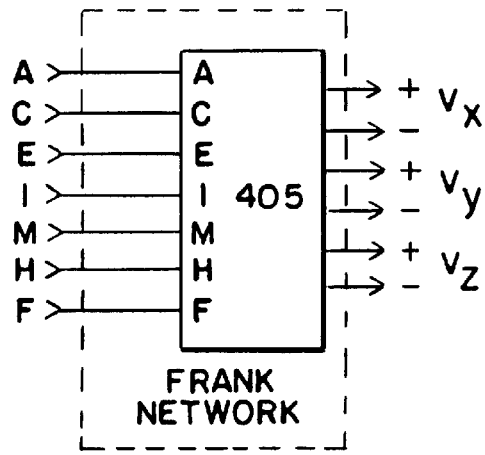
FIG. 5(b) representationally depicts the Frank network as shown in FIG. 5(a), but with a normal (prior art) input configuration to receive signals from conventionally positioned E, M, I, A, C, F and H electrodes as taught by Frank.

When the EASI electrode system is used as the input to the Frank network as shown in FIG. 5(a), the I electrode serves as the reference. (It should be noted that the selection of the I position cis the reference is not essential. Any one of the four EASI electrode positions may serve as the reference). With the I position as the reference, there are three input potential differences $V_{AI}$, $V_{EI}$ and $V_{SI}$ as sensed between electrode pairs A-I, E-l and S-I, respectively. The input/output signal relationship of the Frank network with the input configuration modified as shown in FIG. 5(a) becomes:

$$V_x' = 0.610 V_{AI} + 0.171 V_{EI}$$

$$V_y' = 0.354 V_{AI} - 1.000 V_{SI}$$

$$V_z' = 0.869 V_{AI} - 0.605 V_{EI}$$

The signals produced, herein are referred to as x'y'z' signals (illustrated as voltage signals $V_{x'}$, $V_{y'}$ and $V_{z'}$ in FIG. 5(a)), contain sufficient information to derive xyz vectorcardiographic signals. The accessability of this information is enhanced by good signal strengths and low noise ratios associated with the EASI electrode positions on a subject's body.

It is of course key to the present invention that such information is present and extractable from signals sensed by the EASI electrodes. Also key is the ascertainment of transformation coefficients which enable one to take EASI electrode signals and produce xyz vectorcardiographic and/ or electrocardiographic signals. In the case of signal processor 400 shown in FIG. 4, signals x'y'z' essentially act as a "given" and the transformation or "correction" to xyz signals is performed by correcting network 402, the circuit design of which is shown in FIG. 7.

Figure 7:
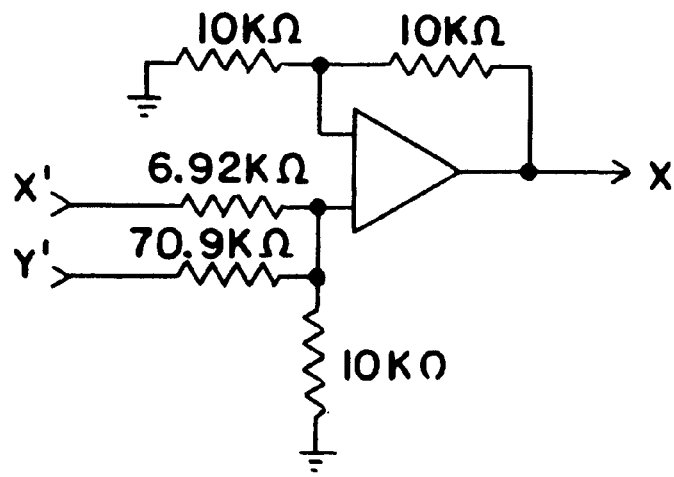
FIG. 7 is a circuit diagram of linear transformation circuits that form correcting network 402.
Figure 7:
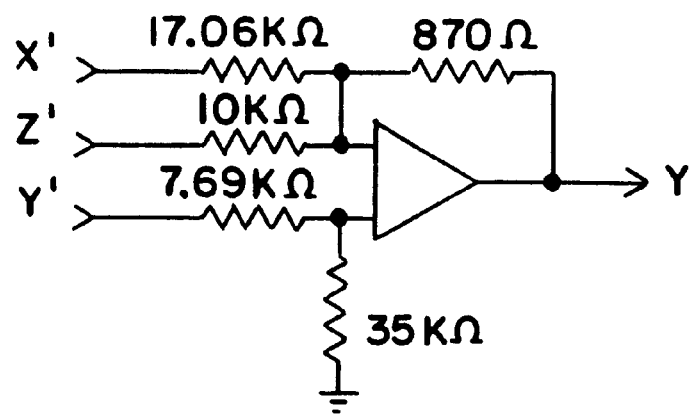
Figure 7:
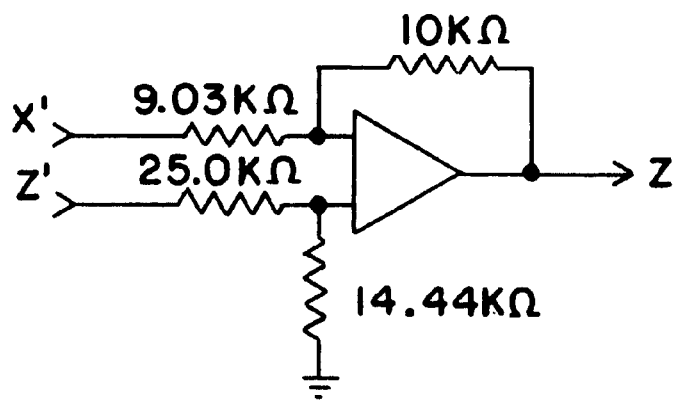

Each of the three circuits shown in FIG. 7, are basic operational amplifier circuits designed to perform linear input/output transformations. As an aside, it should be noted that the input act as voltage sources and are assumed in FIG. 7 to be ideal sources having zero impedance. In practice, this will not be the case. Typically, it will be 100Ω and this value has been assumed as part of the input resistor values shown in FIG. 7. Thus, 100Ω must be subtracted from the resistor values shown in FIG. 7 to obtain the actual resistance values of discrete input resistors.

From the resistor values shown in FIG. 7, it may be readily determined that the three circuits shown will perform to solve the following three equations:

$$V_x = 1.118 V_x' + 0.109 V_z' \quad (10)$$

$$V_y = -0.051 V_x' + 0.933 V_y' 0.087 V_z' \quad (2)$$

$$V_z = -1.108 V_x' + 0.772 V_z' \quad (3)$$

where x, y and z are xyz vectorcardiographic signals. However, implementation of the present invention does not start with the foregoing equations or with the equation solving circuits show in FIG. 1; it starts with a determination of what the coefficients in the foregoing equations should be, and then proceeds with the routine design of circuitry which operates to solve the equations.

A statistical method of determining such coefficients has been devised, and has been found to work remarkably well. Both x'y'z' and xyz signals are sampled at corresponding times from a number of subjects. With the aid of a computer, the samples may be compared using standard least-square methods to extract correlating coefficients. The resulting equations express x, y and z in terms of x', y' and z'.

Because the application of electrodes for stress testing requires careful preparation of the skin, and because the electrodes are used only once, the requirement of only five EASI electrodes (including a ground electrode), connected with the ten normally needed, results in a saving of time and money. Furthermore, by reason of their location favoring large signals and relatively small amounts of movement artifact or signal noise, the quality of the tracings obtained tends to be improved. These benefits can be obtained without modification to existing equipment. However, it will be appreciated that with suitable equipment a variety of displays (including vectorcardiography and polarcardiography) becomes obtainable from xyz signals without modifying the recording technique—the record in all cases being taken from EASI electrode positions.

It will also be apparent to those skilled in the art that the discrete elements represented by Frank network 405 in FIG. 5(a) and the active resistive circuits shown in FIG. 7 can be condensed to provide a more direct derivation of xyz signals from the EASI electrode signals which are the input to network 403. This would forego the immediate advantage of utilizing a commercially available recorder, but recognized that the overall network can readily be condensed and embodied in a single patient's cable. The same is true if one extends the process to include circuitry of surrogate patient device 403.

Although a particular embodiment of the invention has been described in detail for purposes of illustration, various modifications may be made without departing from the spirit and scope of the invention. Accordingly, the invention is not to be limited, except as by the appended claims.

We claim:

1. Instrumentation for measuring arid processing voltages produced by a human heart as sensed between selected points on the surface of a subject's body, said instrumentation comprising:

(a) a first electrode attachable to the anterior midline of the subject's body at a level selected from the group consisting of:
        (i) the fourth rib interspace;
        (ii) the fifth rib interspace;
    (b) second and third electrodes attachable to the subject's body on opposed sides of the anterior midline below the level selected from the group consisting of the fourth rib interspace and the fifth rib interspace, but high enough so they are positioned over the subject's ribs or intercostal spaces;
    (c) a fourth electrode attachable over the subject's manubrium sterni; and,
    (d) signal processing means operatively connected to said electrodes for receiving first, second and third electrical signals present between said first, second and third electrodes as produced by said heart at said points of attachment, and for combining and scaling said signals to produce xyz vectorcardiographic signals in response thereto.

2. Instrumentation as defined in claim 1, wherein the second and third electrodes are positioned at the mid-axillary line.

3. Instrumentation as defined in claim 2, wherein the second and third electrodes are positioned 2.5 centimeters below the level of the first electrode.

4. Instrumentation as defined in claim 1, including a ground electrode operatively connected to said signal processing means and attachable to a preselected location on the subject's body.

5. Instrumentation as defined in claim 4, wherein said preselected location is on the subject's chest.

6. Instrumentation as defined in claim 1, said signal processing means including means for receiving said vectorcardiographic signals and for producing electrocardiographic output signals corresponding to lead signals I, II, III, aVR, aVL, aVF, V1, V2, V3, V4, V5 and V6 of a 12-lead electrocardiogram in response thereto.

7. Instrumentation for measuring and processing voltages produced by a human heart as sensed between selected points on the surface of a subject's body, said instrumentation comprising:

(a) a first electrode attachable to the anterior midline of the subject's body at a level selected from the group consisting of:
        (i) the fourth rib interspace;
        (ii) the fifth rib interspace;
    (b) second and third electrodes attachable to the subject's body on opposed sides of the anterior midline below the level selected from the group consisting of the fourth rib interspace and the fifth rib interspace, but high enough so they are positioned over the subject's ribs or intercostal spaces;
    (c) a fourth electrode attachable over the subject's manubrium sterni; and,
    (d) signal processing means operatively connected to said electrodes for receiving first, second and third electrical signals present between first, second and third pairs of said electrodes as produced by said heart at said points of attachment, and for producing electrocardiographic output signals corresponding to lead signals I, II, III, aVR, aVL, aVF, V1, V2, V3, V4, V5 and V6 of a 12-lead electrocardiogram in response thereto.

8. Instrumentation as defined in claim 7, wherein the second and third electrodes are positioned at the mid-axillary line, 2.5 centimeters below the level of the first electrode.

9. Instrumentation as defined in claim 8, including a ground electrode operatively connected to said signal processing means and attachable to a preselected location on the subject's body.

10. A method of sensing and analyzing activity of a human heart comprising the steps of:

(a) sensing voltage signals generated by the human heart between four electrodes positioned on the surface of a subject's body at, respectively,
(i) the anterior midline of the subject's body at a level selected from the group consisting of:
(A) the fourth rib interspace;
(B) the fifth rib interspace;
(ii) opposed sides of the anterior midline of the subject's body below the level selected from the group consisting of the fourth rib interspace and the fifth rib interspace, but high enough to be positioned over the subject's ribs or intercostal spaces;
(iii) over the manubrium sterni of the subject's body; and, (b) combining and scaling such voltage signals to produce electrocardiograph output signals corresponding to lead signals I, II, III, aVR, aVL, aVF, V1, V2, V3, V4, V5 and V6 of a 12-lead electrocardiogram.

11. A method as defined in claim 10, wherein the step of sensing voltage signals on opposed sides of the interior midline of the subject's body includes the step of doing so at the mid-axillary line, 2.5 centimeters below the level selected from the group consisting of the fourth rib interspace and the fifth rib interspace.

12. A method as defined in claim 10, further comprising the steps of:

(c) combining and scaling said voltage signals to first produce xyz vectorcardiographic signals; and, (d) combining and scaling said xyz vectorcardiographic signals to produce said electrocardiographic output signals.

13. A method of sensing and analyzing activity of a human heart comprising the steps of:

(a) sensing voltage signals generated by the human heart between four electrodes positioned on the surface of a subject's body at, respectively,
(i) the anterior midline of the subject's body at a level selected from the group consisting of:
(A) the fourth rib interspace;
(B) the fifth rib interspace;
(ii) opposed sides of the anterior midline of the subject's body below the level selected from the group consisting of the fourth rib interspace and the fifth rib interspace, but high enough to be positioned over the subject's ribs or intercostal spaces;
(iii) over the manubrium sterni of the subject's body; and, (b) combining and scaling such voltage signals to produce xyz vectorcardiographic output signals.

14. A method as defined in claim 13, wherein the step of sensing voltage signals on opposed sides of the interior midline of the subject's body includes the step of doing so at the mid-axillary line, 2.5 centimeters below the level selected from the group consisting of the fourth rib interspace and the fifth rib interspace.

* * * * *